United States Patent
Wang et al.

(10) Patent No.: US 6,588,283 B2
(45) Date of Patent: Jul. 8, 2003

(54) FRACTURE TOUGHNESS DETERMINATION USING SPIRAL-GROOVED CYLINDRICAL SPECIMEN AND PURE TORSIONAL LOADING

(75) Inventors: Jy-An Wang, Oak Ridge, TN (US); Kenneth C. Liu, Oak Ridge, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 0 days.

(21) Appl. No.: 09/888,937

(22) Filed: Jun. 25, 2001

(65) Prior Publication Data

US 2003/0024323 A1 Feb. 6, 2003

(51) Int. Cl.[7] .......................... G01N 3/26; G01N 19/08
(52) U.S. Cl. ........................................ 73/847; 73/799
(58) Field of Search .................... 73/847, 848, 787, 73/87, 150 A, 799

(56) References Cited

U.S. PATENT DOCUMENTS

| | | | | |
|---|---|---|---|---|
| 2,617,293 A | * | 11/1952 | Schnadt | 73/844 |
| 3,680,367 A | * | 8/1972 | Krafft | 73/799 |
| 4,090,489 A | * | 5/1978 | Barker | 125/13.01 |
| 4,116,049 A | * | 9/1978 | Barker | 73/87 |
| 4,198,870 A | * | 4/1980 | Barker et al. | 73/799 |
| 4,299,120 A | * | 11/1981 | Barker | 73/799 |
| 4,480,826 A | * | 11/1984 | Kaneko | 271/103 |
| 4,821,577 A | * | 4/1989 | Thiercelin et al. | 73/152.11 |
| 4,895,027 A | * | 1/1990 | Manahan, Sr. | 73/794 |

OTHER PUBLICATIONS

Sweeney, J. "Analysis of a Proposed Method for Toughness Measurements Using Torsion Testing", Journal of Strain Analysis, 1685, vol. 20, No. 1, p. 1–5.*

Sweeney, J., "Analysis of a Proposed Method for Toughness Measurements Using Torsion Testing," *Journal of Strain Analysis*, 1985, vol. 20, No. 1, pp. 1–5.

Wang, J. A., Liu, K. C., McCabe, D. E., and David, S. A., "Using Torsional Bar Testing to Determine Fracture Toughness," *Journal of Fatigue & Fracture for Engineering Materials and Structures*, 2000, vol. 23, pp. 917–927.

* cited by examiner

Primary Examiner—Hezron Williams
Assistant Examiner—Lilybett Martir
(74) Attorney, Agent, or Firm—James M. Spicer

(57) ABSTRACT

A method for determining fracture toughness $K_{IC}$ of materials ranging from metallic alloys, brittle ceramics and their composites, and weldments. A cylindrical specimen having a helical V-groove with a 45° pitch is subjected to pure torsion. This loading configuration creates a uniform tensile-stress crack-opening mode, and a transverse plane-strain state along the helical groove. The full length of the spiral groove is equivalent to the thickness of a conventional compact-type specimen. $K_{IC}$ values are determined from the fracture torque and crack length measured from the test specimen using a 3-D finite element program (TOR3D-KIC) developed for the purpose. In addition, a mixed mode (combined tensile and shear stress mode) fracture toughness value can be determined by varying the pitch of the helical groove. Since the key information needed for determining the $K_{IC}$ value is condensed in the vicinity of the crack tip, the specimen can be significantly miniaturized without the loss of generality.

32 Claims, 14 Drawing Sheets

Front View
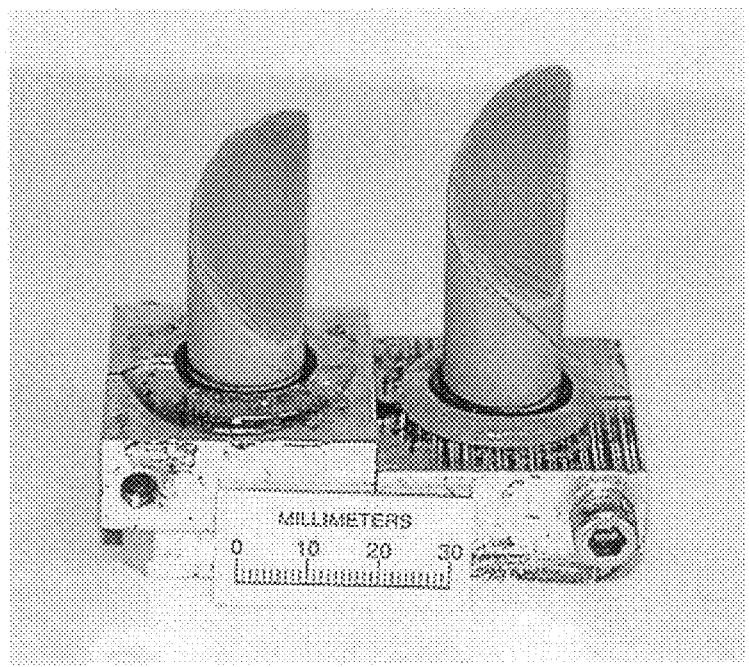
Side View
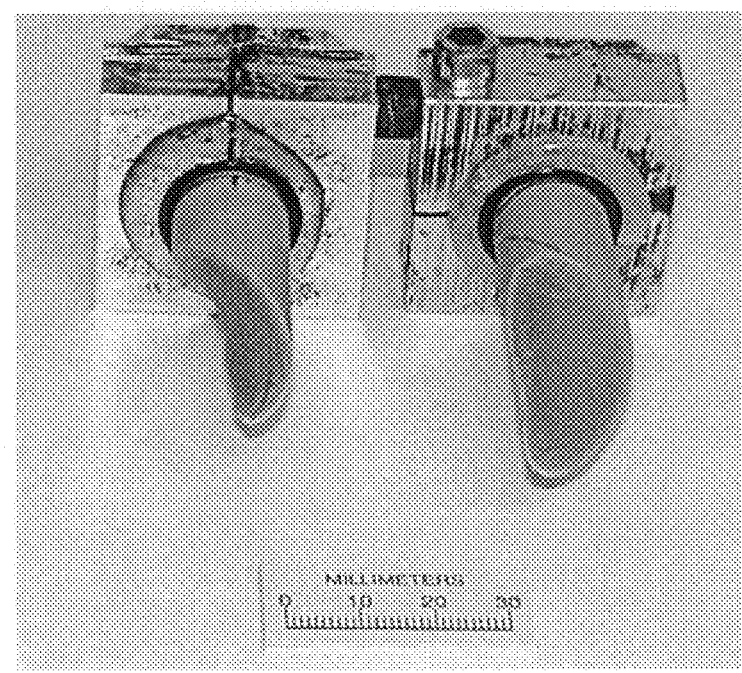
FIG. 5

Front View Side View

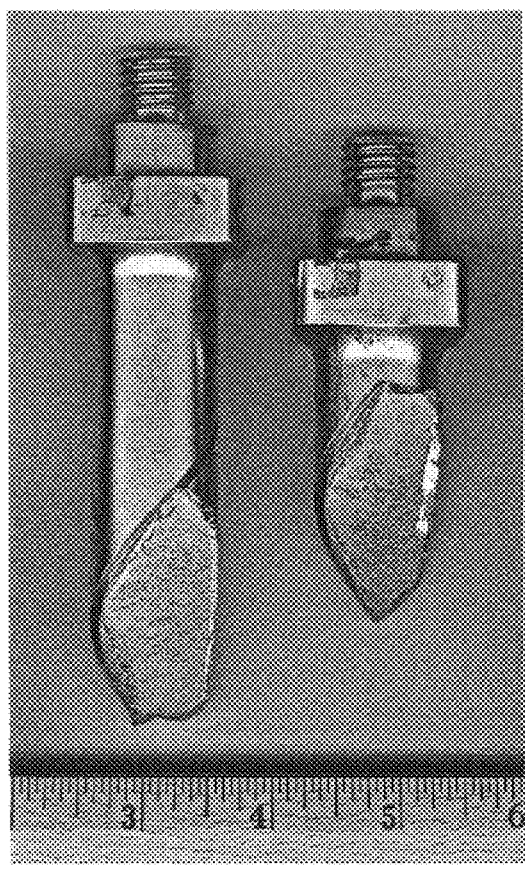 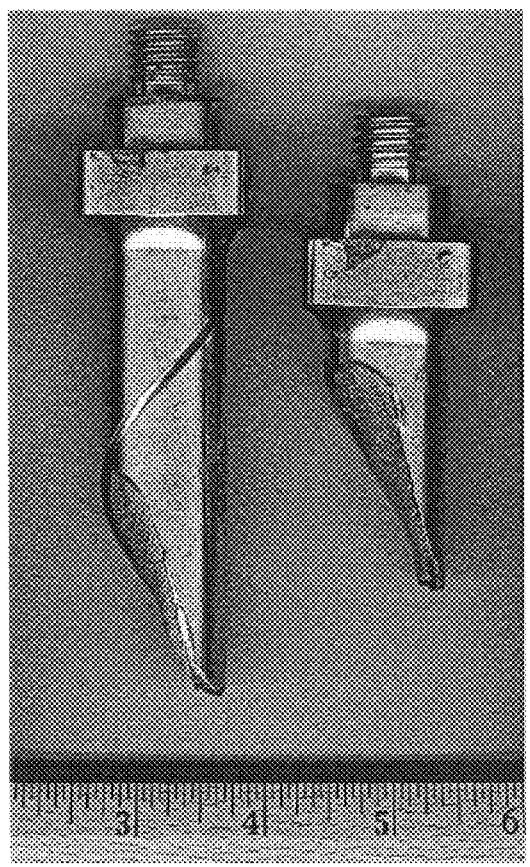
Front View        Side View
FIG. 12

FRACTURE TOUGHNESS DETERMINATION USING SPIRAL-GROOVED CYLINDRICAL SPECIMEN AND PURE TORSIONAL LOADING

STATEMENT REGARDING FEDERALLY SPONSORED RESEARCH OR DEVELOPMENT

The United States Government has rights in this invention pursuant to Contract No. DE-AC05-00OR22725 between the United States Department of Energy and UT-Battelle, LLC.

BACKGROUND OF THE INVENTION

1. Field of the Invention

This invention relates to methods and apparatus for determining the intrinsic values of fracture toughness $K_{IC}$ and mixed mode fracture toughness for various structural materials such as steels, aluminum alloy, ceramics and metal-matrix composites using small spiral-grooved cylindrical specimens and pure torsional loading.

2. Background Information

The present invention determines fracture toughness $K_{IC}$ and mixed mode fracture toughness of solid materials utilizing a unique specimen design and loading condition in conjunction with a special finite element program. $K_{IC}$ is a material property that describes the material's fracture resistance to brittle fracture initiation under full lateral constraint during static or "quasistatic" loading. The test methods that are currently used in many industries, including the nuclear industry, to evaluate fracture toughness may not fully conform to fracture mechanics theory. This is because the specimen size required to achieve complete control of the plane strain is prohibitively large. Hence, when critical flaw size and/or safe design stress is desired, $K_{IC}$ may be inferred from values derived from non-fracture-mechanics methods. Because the indirect methods inevitably contain large uncertainties, a large safety factor must be built into the design. With the invention, $K_{IC}$ is determined directly, without interpretation, allowing the uncertainty and safety factor associated with the safety assessment of fracture properties to be minimized.

In the present invention, a right cylindrical specimen having a spiral groove with a 45° pitch is tested under pure torsion. A computer code, TOR3D-KIC, is then used to determine the mode I fracture toughness. Mixed mode fracture toughness values can be derived by varying the spiral pitch. TOR3D-KIC uses three-dimensional finite element techniques to analyze the crack tip opening displacement (CTOD) occurring on a non-coplanar 3-D spiral crack front. Special 3-D finite element meshes, with wedge singular elements at the crack front, were designed to simulate the 3-D spiral crack front and crack propagation orientation during transition phases of fatigue crack growth and the final fracture. Boundary conditions were assigned for the torsional loading configuration. Based on the input of the fracture load and final crack length, the CTOD at the crack flange along the crack front is analyzed and then integrated into the mode I fracture toughness formulation in conjunction with the minimum strain energy criteria.

The method can be used to determine the fracture toughness of graduated materials such as weldments and their heat-affected zones. Thus, the new method should be invaluable for the development of new structural materials and new welding technology, and it can be used in establishing new industry standards and regulatory guidelines.

The testing method that uses conventional compact tension specimens or their variations has a strong theoretical basis for use in determining fracture toughness, $K_{IC}$. However, the downside of the method is the specimen size effect. Valid test result according to ASTM Test Method for Plane-Strain Fracture Toughness of Metallic Materials (E399), requires that both specimen thickness, B, and crack length, a, exceed $2.5(K_{IC}/\sigma_{YS})^2$, where $\sigma_{YS}$ is the 0.2% offset yield strength of the material for temperature and loading rate of the test. If it is not possible to make a specimen from the available material that meets the criterion, then it is not possible to make a valid $K_{IC}$ measurement according to this method.

One prior method [Ref. 1] for $K_{IC}$ measurement under torsion uses a round specimen with a half penny-shaped crack making a 45° angle with the specimen axis. This is basically a variation of tensile testing with a half penny shaped crack perpendicular to the tensile force. The latter type has been widely used in crack growth studies.

Our recent study [Ref. 2] demonstrated that the specimen size effects could be virtually eliminated using a cylindrical specimen subjected to pure torsion for $K_{IC}$ measurements.

REFERENCES

[1] Sweeney, J., "Analysis of a Proposed Method for Toughness Measurements Using Torsion Testing," *Journal of Strain Analysis*, 1985, Vol. 20, No. 1, pp. 1–5.

[2.] Wang, J. A., Liu, K. C., McCabe, D. E., and David, S. A., "Using Torsional Bar Testing to Determine Fracture Toughness," *Journal of Fatigue & Fracture for Engineering Materials and Structures*, 2000, Vol. 23, pp. 917–927.

BRIEF SUMMARY OF THE INVENTION

In a first embodiment of the invention, a method of determining fracture toughness $K_{IC}$ of a material comprises the steps of providing a cylindrical specimen having a helical groove at a 45° pitch, applying pure torsion to the specimen, measuring the fracture torque, measuring the crack length, and calculating $K_{IC}$ from the fracture torque and the crack length.

The calculation of $K_{IC}$ is carried out with a computer program which comprises the steps of: establishing a finite element mesh for a cylindrical specimen under pure torsion to generate an equibiaxial tension/compression stress field on ±45°-pitched orthogonal planes of the finite elements along the right conoids, and a plane strain condition is maintained on every plane normal to the helical groove; establishing 3-D isoparametric finite element meshes with singular elements around the 3-D spiral crack front to simulate $r^{-\frac{1}{2}}$ singularity at the crack tip; simulating spiral crack front and crack propagation orientation along the right conoids; prescribing boundary conditions with free axial displacement to simulate pure torsion loading; applying initial end rotation to the finite element model with a given final crack length to determine the corresponding end torque; iterating the end torque step to match the end torque with the measured fracture torque to determine the final end rotation of the finite element model; determining the crack tip opening displacement based on the stress/strain field derived from the calculated final end rotation; verifying that the triaxial stresses and T-stress fields around the crack tip at fracture are positive to ensure a high constraint state is achieved; determining stress intensity factors $K_I$, $K_{II}$, and $K_{III}$ from the crack tip opening displacement; and utilizing the stress intensity factors $K_I$, $K_{II}$, and $K_{III}$ information and strain energy density criteria to determine the fracture toughness $K_{IC}$.

In a second embodiment of the invention, a method of determining mixed mode fracture toughness of a material comprises the steps of providing a cylindrical specimen having a helical groove, applying pure torsion to the specimen, measuring the fracture torque, measuring the crack length, and calculating the mixed mode fracture toughness from the fracture torque and the crack length.

The calculation of mixed mode fracture toughness is carried out with a computer program which comprises the steps of: establishing a finite element mesh for a cylindrical specimen under pure torsion to generate an equibiaxial tension/compression stress field on ±45°-pitched orthogonal planes of the finite elements along the right conoids, and a plane strain condition is maintained on every plane normal to the helical groove; establishing 3-D isoparametric finite element meshes with singular elements around the 3-D spiral crack front to simulate $r^{-\frac{1}{2}}$ singularity at the crack tip; simulating spiral crack front and crack propagation orientation along the right conoids; prescribing boundary conditions with free axial displacement to simulate pure torsion loading; applying initial end rotation to the finite element model with a given final crack length to determine the corresponding end torque; iterating the end torque step to match the end torque with the measured fracture torque to determine the final end rotation of the finite element model; determining the crack tip opening displacement based on the stress/strain field derived from the calculated final end rotation; verifying that the triaxial stresses and T-stress fields around the crack tip at fracture are positive to ensure a high constraint state is achieved; determining stress intensity factors $K_I$, $K_{II}$, and $K_{III}$ from the crack tip opening displacement; and utilizing the stress intensity factors $K_I$, $K_{II}$, and $K_{III}$ information and strain energy density criteria to determine the mixed mode fracture toughness.

BRIEF DESCRIPTION OF THE DRAWINGS

FIG. 2a shows the cylindrical specimen with a V-grooved spiral line with a 45° pitch. FIG. 2b shows that when the grooved specimen is sectioned into segments perpendicular to the groove line, defined as the Z-axis, each of the segments can be viewed as a CT specimen with a notch as illustrated in FIG. 2c. FIG. 2d shows the stress state of a generic element in a cylindrical bar under pure torsion in the absence of the V-groove. FIG. 2e shows the axis notation for the notch root area.

FIG. 5 shows a broken mullite ceramic specimen with a 0.02-inch deep spiral V-notch.

FIG. 12 shows a broken 7475 aluminum specimen with 0.075-inch deep spiral V-notch and 0.23-inch deep fatigue precrack.

DETAILED DESCRIPTION OF THE INVENTION

Figure 1:
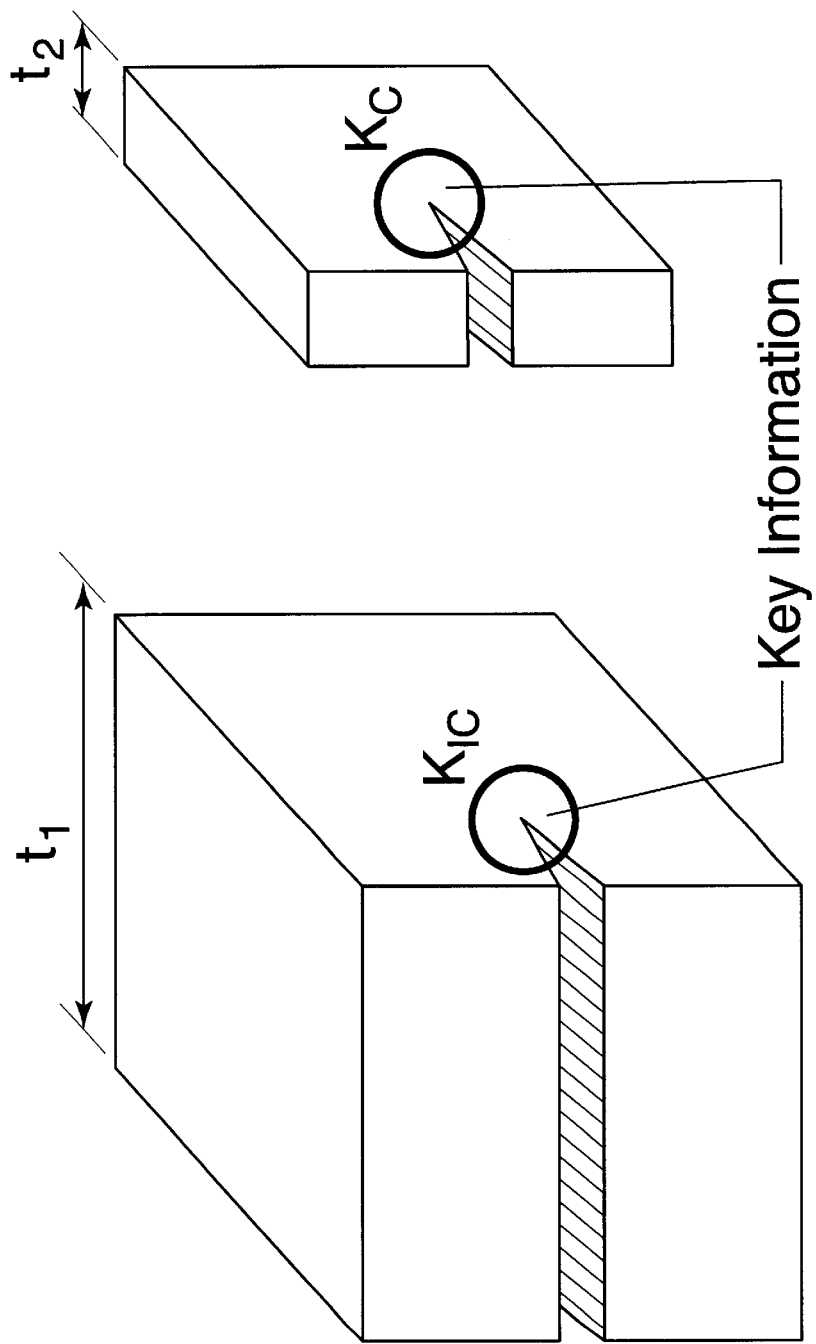
FIG. 1 illustrates the specimen size effect with conventional compact type specimens.

Valid fracture toughness of solid materials must be measured in the stress and strain fields conforming to the requirements of fracture mechanics theory. FIG. 1 shows two compact-tension (CT) specimens having the same profile but different thickness. In theory, an ideal plane strain condition is achieved for a valid $K_{IC}$ measurement if the specimen with $t_1$ has an infinite thickness. This is impractical. However, a reasonably accurate value can be obtained and acceptable if the requirements cited in ASTM Standard E399 are met. Basically, E399 recommends what minimum thickness is required for a compact type specimen to yield an acceptable $K_{IC}$ value that can be obtained in a practical manner. A violation of the plane strain condition in the critical stress zone near the crack tip of the thin specimen will not yield a valid $K_{IC}$ value but a critical stress intensity factor, $K_c$.

Figure 4:
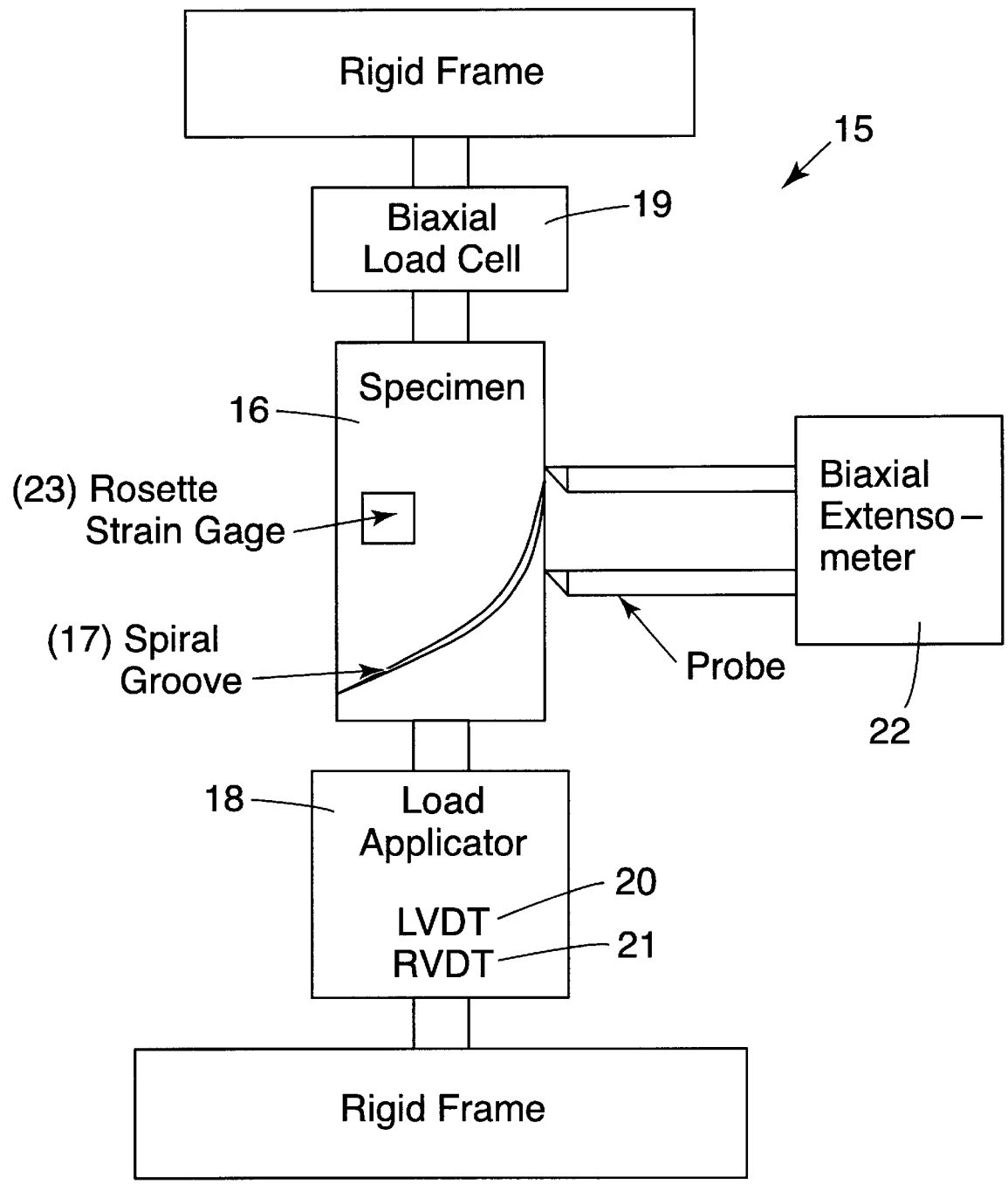
FIG. 4 shows the experimental set-up for torsion testing of specimens of both embodiments of the present invention, illustrating a biaxial extensometer and a strain gage located at a 45° angle to the axial orientation.

Reference is now made to FIG. 4, which shows a biaxial testing system 15 and also illustrates one embodiment of the present invention. In FIG. 4, a cylindrical specimen 16 is prepared with a 45° pitch, spiral V-groove 17 machined on the uniform section of the specimen surface, the pitch extending at least one half turn in order to minimize end effects. When pure torsion (with zero axial load) is applied to the specimen 16 by the load applicator 18, an equibiaxial tension/compression stress field is generated on the ±45°-pitched orthogonal planes that intersect along the right conoids (perpendicular to the center axis of the cylindrical specimen 16 under pure torsion loading). The specimen 16 is a different manifestation of a CT specimen having a thickness equivalent to the total length of the helical or spiral groove 17 when the cylindrical surface is unwrapped. Due to the axisymmetry of the grooved cylindrical specimen 16, the plane strain requirement along the spiral groove (or notch) 17 is satisfied.

Also in FIG. 4, the biaxial testing system 15 is equipped with an axial/torsional biaxial load cell 19, a linear variable differential transformer (LVDT) 20 to monitor and control the axial displacement, and a rotational variable differential transformer (RVDT) 21 to measure and control the angular displacement. Shear strain is measured using an axial/torsional biaxial extensometer 22 and a Rosette strain gage 23 to cross check the accuracy. Postmortem examination of the tested specimens is also used to verify that a high constraint state is effectively achieved.

The computer code, discussed earlier, is used with both embodiments of the present invention. The TOR3D-KIC computer code was developed to simulate the 3-D spiral crack front and crack propagation orientation during transition phases of fatigue crack growth and the final fracture under pure torsion loading. TOR3D-KIC is used as a means to calculate mode I fracture toughness of solid materials, using the cylindrical specimen having a prefabricated spiral V-grooved line with a 45° pitch on the specimen surface. Mixed mode fracture toughness values in various combinations of mode I, II, and III, are derived by varying the spiral pitch. TOR3D-KIC uses three-dimensional finite element techniques to analyze the crack tip opening displacement (CTOD) occurring on a non-coplanar 3-D spiral crack front, where 3-D wedge singular elements are used adjacent the crack front to simulate $r^{-\frac{1}{2}}$ stress singularity at the crack tip. Based on the input of the fracture load and final crack length obtained from the torsion fracture testing, the CTODs at the crack flange along the crack front at fracture were analyzed. The stress intensity factors $K_I$, $K_{II}$, and $K_{III}$ are estimated from CTOD, and then integrated into the mode I fracture toughness formulation using minimum strain energy criteria.

Due to the high concentration of stress and strain generated around the notch tip area, key information needed for determining $K_{IC}$ values is densely concentrated near the crack tip zone. The vast area of conventional compact type specimen remote from the crack tip is mainly used to maintain uniform far fields of stress and strain and for specimen gripping to transmit load. Therefore, a small specimen of the proposed method having a diameter 2 to 4 times the plastic process zone will suffice for fracture toughness testing.

Figure 2:
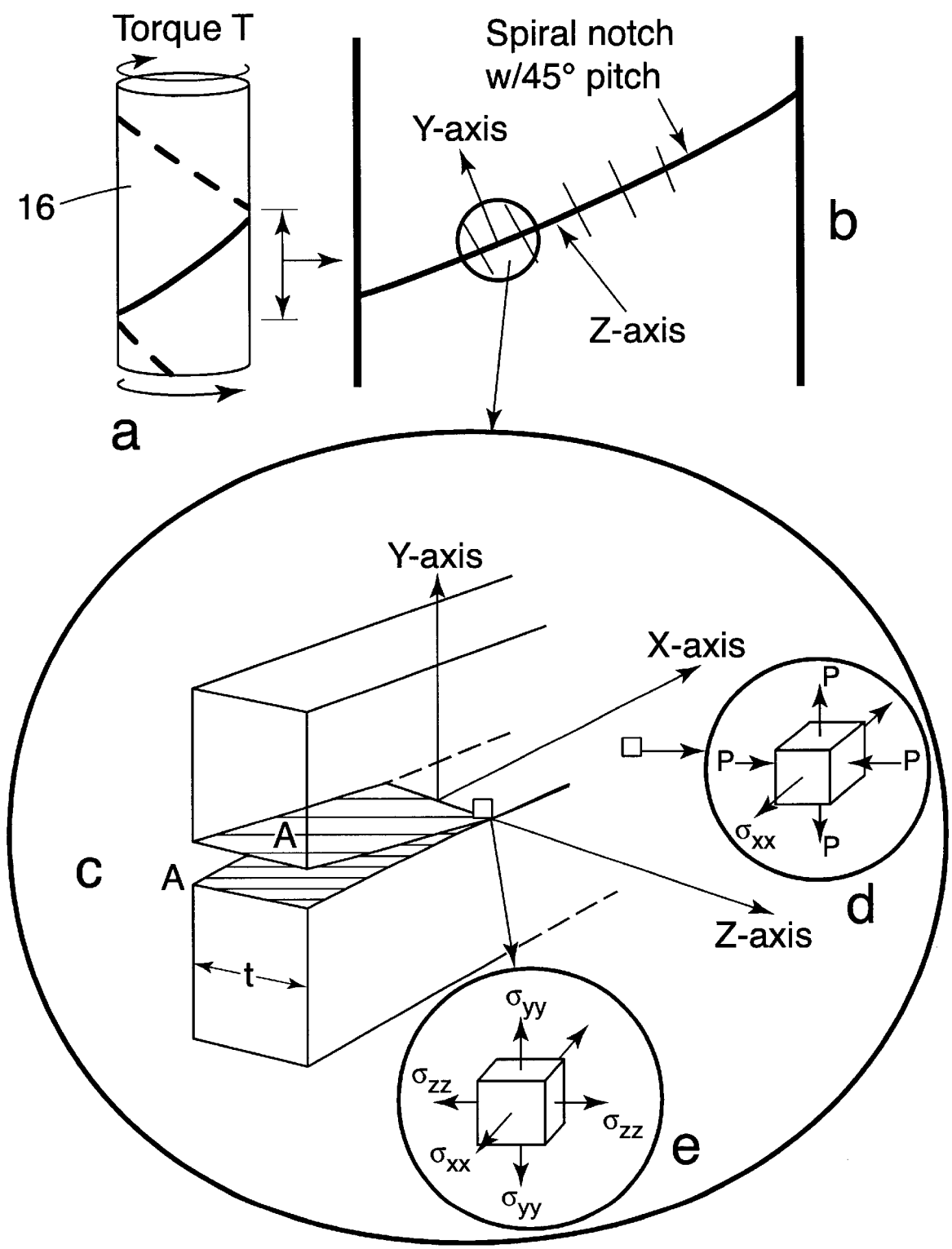
FIG. 2 illustrates the geometry constraint and stress distribution in notch structure for a pure torsion loading condition with a spiral notch pitched at 45° angle.

FIG. 2a also shows the cylindrical specimen 16 with V-grooved spiral line with a 45° pitch. When a specimen with no spiral line is subjected to pure torsion, uniform stress and strain fields are axisymmetrical and constrained along the axis. When the grooved specimen (FIG. 2b) is sectioned into segments perpendicular to the groove line, defined as the Z-axis, each of the segments can be viewed as a CT specimen with a notch as illustrated in FIG. 2c. Since all the imaginary CT specimens are bonded side-by-side seamlessly, the compatibility condition is automatically satisfied in every XY-plane which remains in plane before and after application of torsion loading.

In the absence of the V-groove, the stress state of a generic element in a cylindrical bar under pure torsion can be depicted as shown in FIG. 2d. Here, the XZ-plane is in tension and the XY-plane is in compression of equal magnitude. When a notch is introduced (FIG. 2c), the lateral sides of the wedge along the notch opening line will not contract because the stress in shaded area "A" is relieved. The disappearance of the tensile stress along the notch opening will shift the burden to the root of the notch, where a sharp rise will occur in the tensile $\sigma_{yy}$ component. Since the unstressed area "A" does not contract in the Z-axis direction, while the material ahead of the notch root has a propensity to contract, a tensile stress field will develop in the $\sigma_{zz}$ component in the root area of the notch. The transverse tensile stress $\sigma_{xx}$ developing ahead of the notch front is due to the radial constraint. Therefore, a triaxial tensile stress field will evolve in the neighborhood of the notch root area (see FIG. 2e). This observation has been experimentally and analytically validated and will be discussed in later sections.

The stress and strain fields in any cross section along the axis of the round specimen under pure torsion are the same even though having the groove. Thus, the constraint effect (size effect), normally a concern in compact type specimens, is eliminated. Therefore, this procedure is suitable for miniature specimen testing. It is well known that materials fracture in mixed modes rather than in a single mode; and in many cases, a combination of mode I and mode III may be more detrimental than mode I alone. The present invention method enables any combination of mixed mode by varying the pitch angle.

RESULTS

Figure 3:
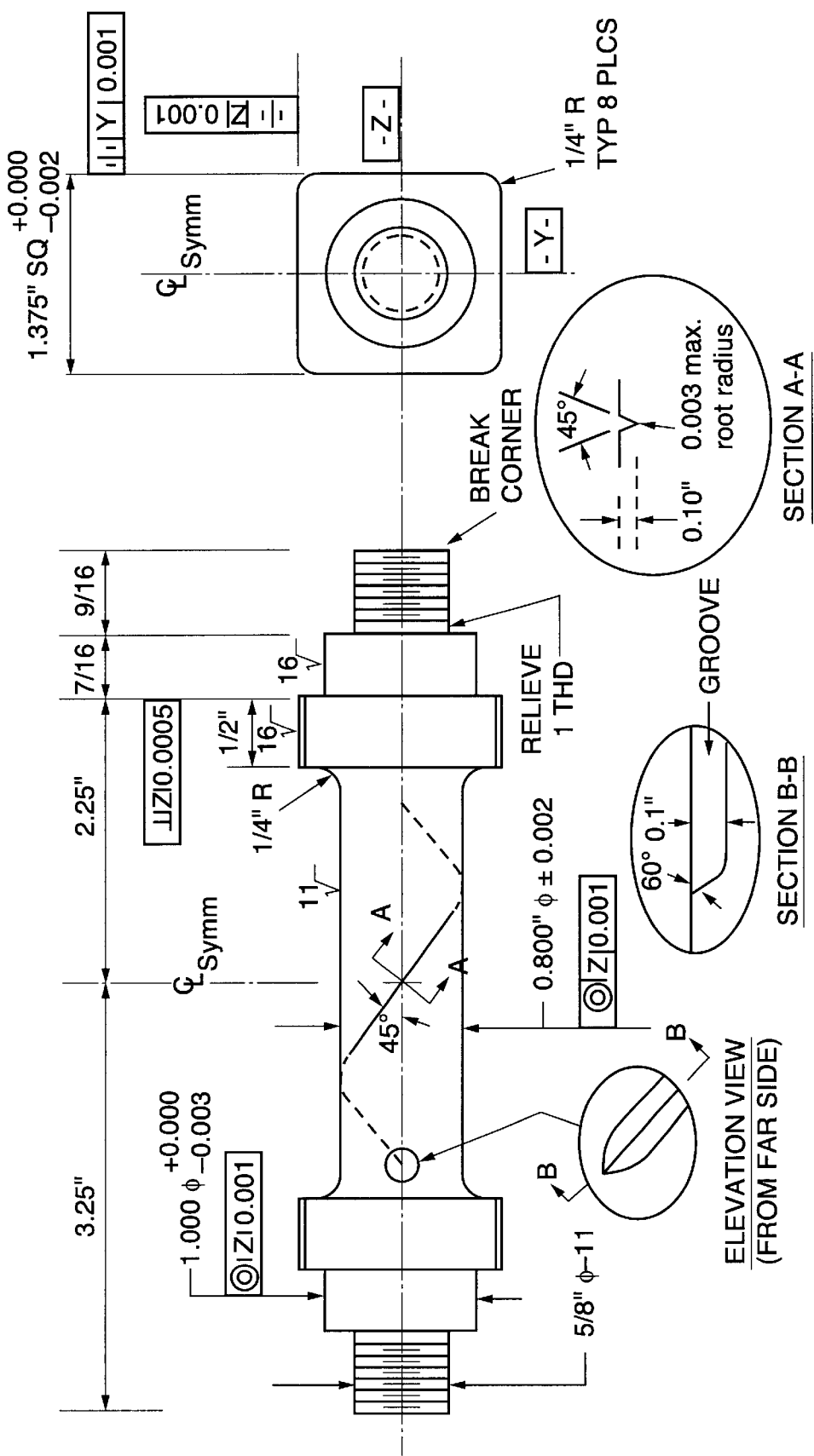
FIG. 3 shows the specimen design configuration for a tested A302B steel specimen.

FIG. 3 shows the geometry of a specimen used in $K_{IC}$ measurements of metallic alloys. The specimen in FIG. 3 has a uniform gage section on which a complete lobe of spiral V-groove with a pitch of 45° is shown for mode I testing. The pitch angle can be tailored for a mixed mode test. The squared end sections were made to transmit torque and the threaded ends for zero axial load control. The size of the test specimen is optional depending on the availability of the material. The specimen shown was fabricated from a block of A302B steel. Other specimens were fabricated from a 2-in. plate of 7475-T7351 aluminum alloy. The reader is referred to reference [1] for experimental details and test results of 7475-T7351 aluminum.

Ceramic materials are usually available in a small volume, and small round rods are most common. Mullite ceramic material was selected for study. A straight mullite ceramic rod, having each end bonded with epoxy adhesive to a square-ended metal holder of the same design used in the metal specimens, was used in the experiment. Due to the brittle nature of ceramic materials, only a shallow spiral notch was required. Torsion tests were performed on the closed-loop controlled, electro-hydraulic, biaxial testing system 15 shown in FIG. 4. Shear strain was measured using the biaxial strain extensometer 22, and the Rosette strain gage 23 was used for cross calibration. Pure torsion was achieved with a controlled zero axial force.

Precracking for metallic specimens was accomplished with cyclic torsion using the Haver sine wave form. The maximum torque used in precracking varies with materials and must be determined experimentally. In the case of A302B steel, 60–80% of the torque that generates the shear stress of 300 MPa around the specimen diameter will suffice. The fatigue crack growth was measured by postmortem examination. Precracking was not needed for the mullite specimen.

Experimental Results for Mullite Ceramic Specimens

Mullite specimens were made of a round rod, having a uniform gage section of 17-mm diameter and 50-mm gauge length. A mullite specimen having a spiral V-groove with a depth of 0.5-mm was tested. The specimen (FIG. 5) failed at 49.67 NXm torque. Postmortem examination indicates that the failure mode is brittle fracture. The $K_{IC}$ was estimated as 2.205 MPa√m from the torsion test and reported as 2.20 MPa √m from vendor's data.

Experimental Results For A302B Steel Specimens

Figure 6:
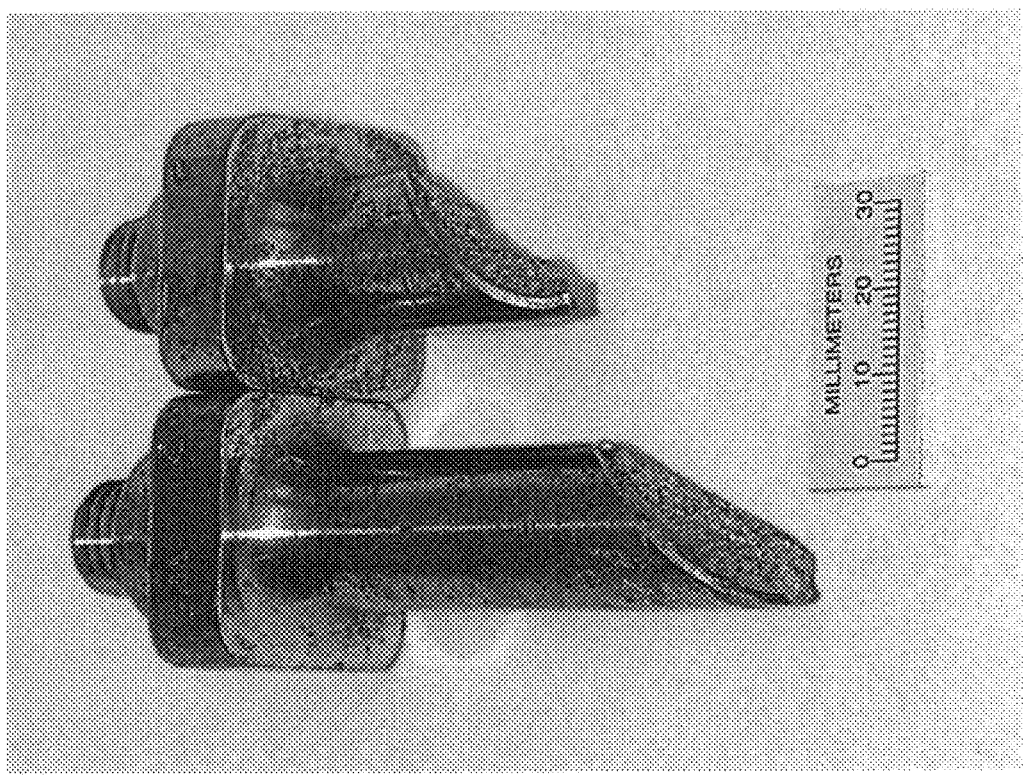
FIG. 6 shows a broken A302B specimen with a 0.075-inch deep spiral V-notch and a 0.2-inch fatigue precrack.
Figure 7:
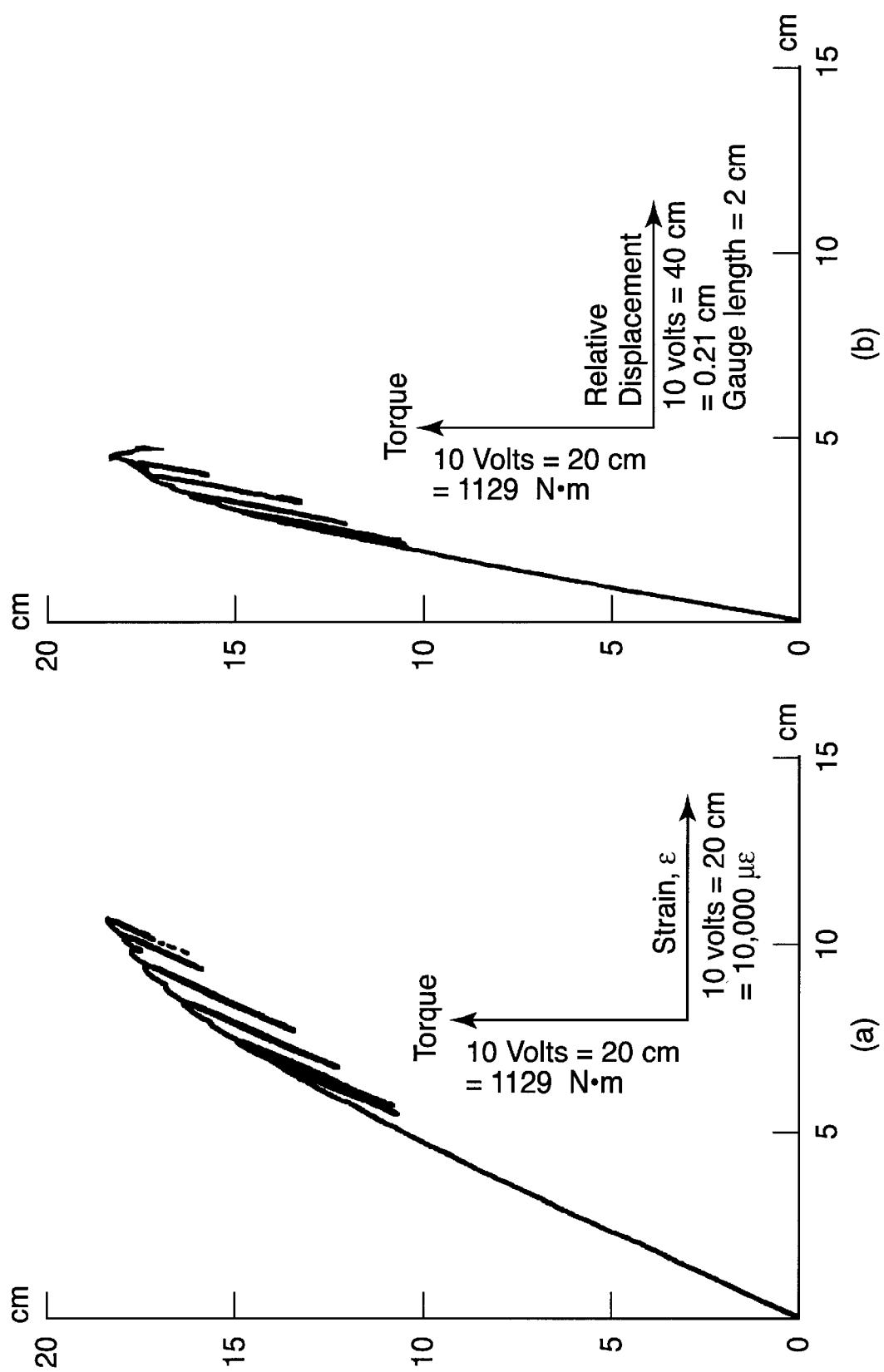
FIG. 7 is a plot of torsion test results from (a) a load cell and strain gauge, and (b) a load cell and biaxial extensometer.

The A302B specimen (FIG. 3) has a uniform gage section of 20.3-mm diameter and 76.2-mm gauge length. A A302B specimen having a spiral V-groove with a depth of 1.9-mm was tested. An exploratory fatigue precrack procedure was used to control crack growth with reference to the change in slope of the load-displacement curves. The specimen fractured at 519.7 NXm torque (FIG. 6). Test results obtained from the strain gage and biaxial extensometer are shown in FIGS. 7a and 7b, respectively. Postmortem examination indicates that the final failure mode is brittle fracture.

When a circular bar is under pure torsion, the neutral axis coincides with the central axis of the bar. Under cyclic torsion, mode I crack propagates perpendicularly toward the central axis due to axisymmetric plane constraint. It is of interest to note that the stress fields at the opposite ends of a diameter (FIG. 2a) are 90° out of phase. Since the stress acting on the XZ-plane (FIG. 2c) at the crack tip is in tension, the stress acting in the same direction at the diametrically opposite end will be in compression. Since the situation is analogous to the stress distribution in a bend beam, the crack extension under the partial unloading/ reloading sequence was estimated utilizing the following equation developed for a three point bending test:

$$\Delta a_i = \Delta a_{i-1} + \left(\frac{b_{i-1}}{\eta_{i-1}}\right)\left(\frac{C_i - C_{i-1}}{C_{i-1}}\right),$$

where $(C_i-C_{i-1})/C_{i-1}$ is the rate change in elastic compliance, $C_i$ represents the elastic compliance of the loading curve of applied torque versus strain measured either from the strain gage or biaxial extensometer. The initial ligament, $b_0$, is equal to the diameter less the notch depth and fatigue precrack. $\eta_i$ is preset to 2. The crack extension occurring during the cyclic torsion was calculated to be 0.33-mm.

The total crack length prior to final brittle fracture was estimated as 7.62 mm. The mode I fracture toughness was estimated to be 55.8 MPa√m. Results of tests on the standard CT specimens made from the same A302B stock yielded an average $K_{IC}$ of 54.9 MPa√m in the TL orientation.

Theoretical Basis of Methodology: Development of Finite Element Models and Analyses PATRAN was used to create three dimensional finite element meshes and ABAQUS was used for analysis. Since the specimen is uniformly loaded in torsion from end to end, a slice of the gage section was modeled and analyzed with appropriate boundary conditions. Prismatic quadratic isoparametric singular elements adjacent to the crack tip are modified to facilitate the computational flexibility in linear elastic and non-linear elastic-plastic fracture mechanics analyses. In the former, the nodes at the crack tip are constrained to have the same displacement in order to embody the $r^{-\frac{1}{2}}$ singularity. However, in the case of perfect plasticity, the nodes at the crack tip are free to displace independently from each other, resulting in inverse (1/r) singularity at the crack tip, and blunting of the crack tip is obtained during loading.

Investigation of Specimen Size Effects for Torsion Bar Testing

It is known that in order to characterize the crack tip fields and plastic zone size occurring uniquely in small-scale yielding conditions, the boundary layer model must include the second term (T-stress) of the Williams expansion as well as the stress intensity factor. The magnitude of T-stress varies with remotely applied stress, and geometry dependence is best indexed by a non-dimensional geometry factor, $\beta$, known as the biaxiality factor which has the form, $$\beta = \frac{T\sqrt{\pi a}}{K}. \quad (2)$$

Due to the very fine mesh required to determine the T-stress, especially in a three-dimensional model, it requires a very large computing power. Thus, the following two simplified approaches were adopted prior size effect studies. In the first, the effect of finite size on opening mode stress, $\sigma_{yy}$, near the crack tip at a constant normalized distance $R=r/(J/\sigma_0)$ ahead of the crack as $$\frac{\sigma_{yy}}{\sigma_0} = \sum_{i=0}^{n} D_i \left(\frac{\beta K}{\sigma_0 \sqrt{\pi a}}\right)^i, \quad (3)$$

where, $D_i$ are the fitting coefficients for a particular set of finite element results and $\sigma_0$ is the reference stress. For $\beta>0$ indicating highly constrained, Eq. 3 predicts a continuous increase of normalized opening mode stress with increasing load. We successfully applied this approach in our size effect study for 7475-T7351 aluminum alloy [Ref. 1].

The other simplified approach suggests that the simplest and most direct method of calculating the biaxiality parameter and, in turn, T-stress is by inspection of the displacement field associated with the crack tip. On the crack flanks, the displacement field can be written as $$u = -(1-v^2)\frac{\beta K}{E\sqrt{\pi a}}r. \quad (4)$$

This allows the biaxiality parameter to be determined directly by inspection of the asymptotic displacement given by Eq. 4.

To apply the boundary layer formulation in 3-D, it is essential that the 2-D displacement field still prescribe the traction along the boundary. It is known that for a 3-D blunt crack with a small curvature the stress and displacement are the same as those of a 2-D notch under plane strain condition. It is also known that in 3-D analysis the biaxiality factor is mostly affected by the stress parallel to the crack flank. Thus, the two approaches formulated in Eqs. 3 and 4 are also valid in the three-dimensional case, and are utilized to determine the constraint effect for the specimen configuration and loading conditions.

Non-Coplanar Crack Propagation Orientation

In many practical situations, structures are subjected to a combination of both shear and tensile/compression loading, which leads to a mixed mode fracture. Three criteria are known for non-coplanar crack growth under mixed mode loading. The first is based on the maximum principal stress and the second on the strain energy density factor. The former postulates that a crack will propagate in a direction perpendicular to the maximum principal stress. The third criterion is based on the energy release rate method. It is postulated that the branch crack propagates in the direction that causes the energy to release at a maximum rate, and that initiation occurs when the value of this energy release rate reaches a critical value. This postulate yields results identical to that of the maximum principal stress theory.

The strain energy density criterion states that crack growth takes place in the direction of minimum strain energy density factor S. The 3-D energy density factor can be written as $$S = a_{11}K_I^2 + 2a_{12}K_IK_{II} + a_{22}K_{II}^2 + a_{33}K_{III}^2, \quad (5)$$

where, $$a_{11} = \frac{1}{16\mu}[(3-4v-\cos\theta)(1+\cos\theta)], \quad (6)$$

$$a_{12} = \frac{1}{8\mu}[\sin\theta(\cos\theta - 1 + 2v)],$$

-continued $$a_{22} = \frac{1}{16\mu}[4(1-v)(1-\cos\theta) + (3\cos\theta - 1)(1+\cos\theta)],$$

$$a_{33} = \frac{1}{4\mu}.$$

The stress intensity factors at the corner nodes of a 3-D finite element model with singular prismatic elements are written as below.

$$K_I = \frac{E}{4(1-v^2)}\left\{\sqrt{\frac{\pi}{2L_1}}\left[\left(\begin{array}{c}2v_B - v_C + 2v_E - v_F + v_D - \\ 2v_{B'} + v_{C'} - 2v_{E'} + v_{F'} - v_{D'}\end{array}\right) + \right.\right.$$

$$\left.\left.\frac{\eta}{2}\left(\begin{array}{c}-4v_B + v_C + 4v_E - v_F + \\ 4v_{B'} - v_{C'} - 4v_{E'} + v_{F'}\end{array}\right) + \frac{\eta^2}{2}\left(\begin{array}{c}v_F + v_C - 2v_D - \\ v_{F'} - v_{C'} + 2v_{D'}\end{array}\right)\right]\right\},$$

$$K_{II} = \frac{E}{4(1-v^2)}\left\{\sqrt{\frac{\pi}{2L_1}}\left[\left(\begin{array}{c}2u_B - u_C + 2u_E - u_F + u_D - \\ 2u_{B'} + u_{C'} - 2u_{E'} + u_{F'} - u_{D'}\end{array}\right) + \right.\right.$$

$$\left.\left.\frac{\eta}{2}\left(\begin{array}{c}-4u_B + u_C + 4u_E - u_F + \\ 4u_{B'} - u_{C'} - 4u_{E'} + u_{F'}\end{array}\right) + \frac{\eta^2}{2}\left(\begin{array}{c}u_F + u_C - 2u_D - \\ u_{F'} - u_{C'} + 2u_{D'}\end{array}\right)\right]\right\},$$

$$K_{III} = \frac{E}{4(1+v)}\left\{\sqrt{\frac{\pi}{2L_1}}\left[\left(\begin{array}{c}2w_B - w_C + 2w_E - w_F + w_D - \\ 2w_{B'} + w_{C'} - 2w_{E'} + w_{F'} - w_{D'}\end{array}\right) + \right.\right.$$

$$\left.\left.\frac{\eta}{2}\left(\begin{array}{c}-4w_B + w_C + 4w_E - w_F + \\ 4w_{B'} - w_{C'} - 4w_{E'} + w_{F'}\end{array}\right) + \frac{\eta^2}{2}\left(\begin{array}{c}w_F + w_C - 2w_D - \\ w_{F'} - w_{C'} + 2w_{D'}\end{array}\right)\right]\right\}$$

where $\eta = -1$ or $1$ at the corner nodes along the crack front. The crack growth occurs when $$S^* = S_{cr} = \frac{1-2v}{4\mu}K_{IC}^2 \qquad (7)$$

Thus $K_{IC}$ can be written as $$K_{IC} = \qquad (8)$$

$$\sqrt{\left(\frac{4\mu}{1-2v}\right)(a_{11}K_I^2 + 2a_{12}K_IK_{II} + a_{22}K_{II}^2 + a_{33}K_{III}^2)},$$

at $\theta = \theta_0$.

Mixed Modes J-Integral Evaluation

It is also known that the stress intensity factor K and the strain energy release rate G are related. For plane strain mode I, the energy release rate $G_I$ can be written as $$G_I = \frac{K_I^2(1-v^2)}{E}. \qquad (9)$$

and for mode II and mode III as, $$G_{II} = \frac{K_{II}^2(1-v^2)}{E}, \text{ and } G_{III} = \frac{K_{III}^2(1+v)}{E}. \qquad (10)$$

For a mixed mode of fracture, the total energy release rate is written as $$G = G_I + G_{II} + G_{III}. \qquad (11)$$

For a linear elastic material, G can also be related to J-integral as $$J = G \qquad (12)$$

For a 2-D mixed mode problem, it is known that it is possible to decouple the J-integral into mode I and mode II components. This is done by separating the stress, strain, traction, and displacement fields analytically into mode I and mode II components within a symmetric mesh region in the neighborhood of the crack tip. The mode III is normal to and therefore independent of the mode I and II. Based on the above observations, and if the local coordinates coincide with the principal stresses, the J-integral can be written as $$J = J_I + J_{II} + J_{III}. \qquad (13)$$

For a linear elastic fracture mechanics problem in plane strain, $J_i$ can be written as $$J_I = \frac{(1-v^2)K_I^2}{E}, \quad J_{II} = \frac{(1-v^2)K_{II}^2}{E}, \quad J_{III} = \frac{(1+v)K_{III}^2}{E}. \qquad (14)$$

Since the J integral is an energy approach, an elaborated expression of the crack tip singular fields is not necessary. This is due to the small contribution that the crack tip field makes relative to the total J (i.e., strain energy) of the body. The J-integral is calculated using the Contour Integral of ABAQUS, which is based on the domain integral method.

3-D Configuration of Finite Element Model (FEM) Used in Analytical Analyses

Figure 8:
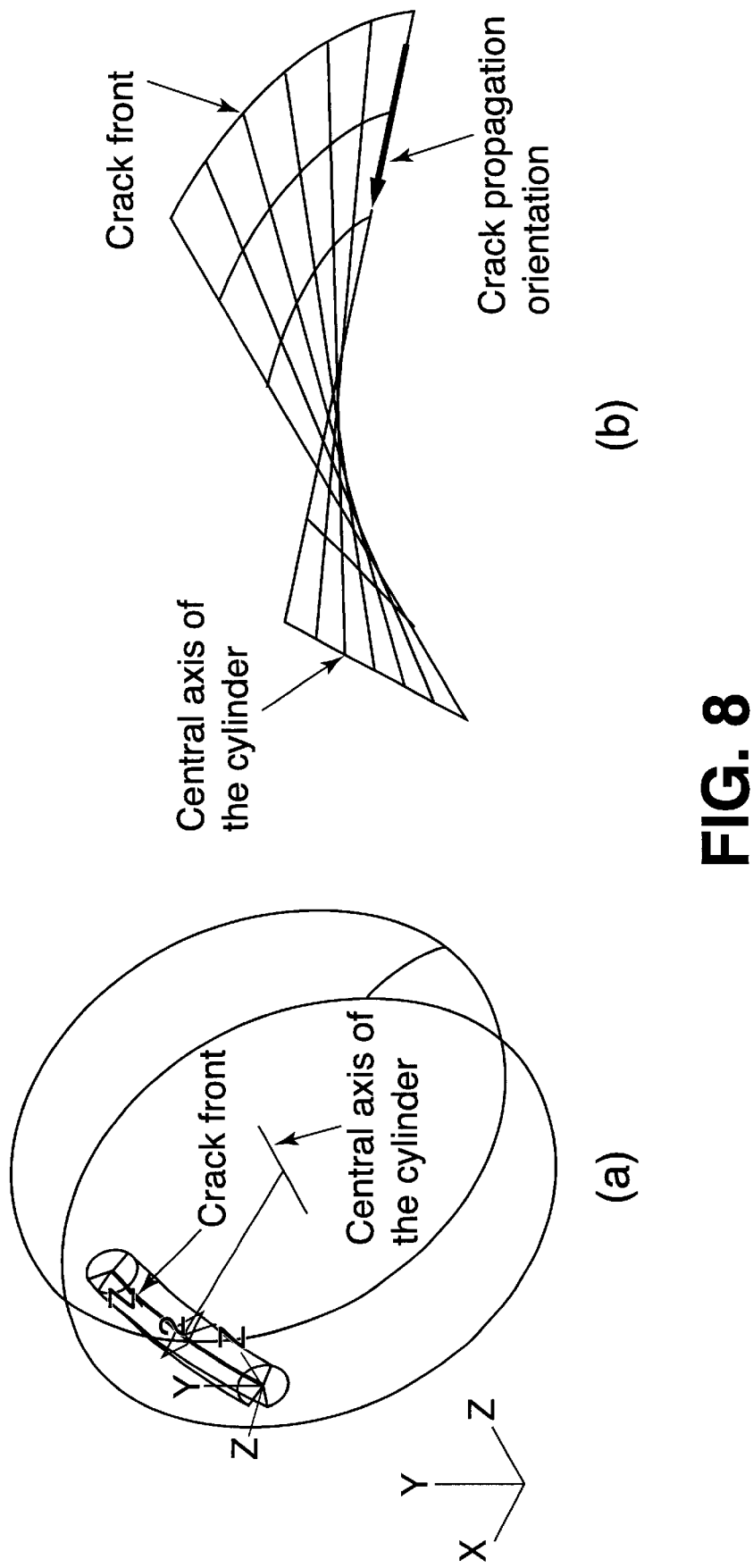
FIG. 8a is a 3-D plot showing the crack propagation orientation at the middle of the crack front.
FIG. 8b is a plot of the fracture surface topology based on the assumption that the crack propagation orientation is perpendicular and points to the central axis of the cylindrical specimen.

FIG. 8a depicts a global and two local Cartesian coordinate systems used to define the orientations of the specimen and a small imaginary cylinder centered at the spiral crack front. The first local coordinate system (a-system) is located at the lower end of the crack front and the second one (b-system) is located at the mid-length of the crack front. The XY plane of the two local coordinates is normal to the crack front. Since the specimen is uniformly twisted along the entire length, it is postulated that the crack propagates in the XZ-plane toward the center axis of the specimen (FIG. 8b). Postmortem examination of fracture surfaces also supports the assumption. Based on this assumption, two different types of finite element meshes were generated, Type I with 45° spiral crack front aligned with the root of the spiral v-groove, and Type II with 45° spiral crack front aligned with the fatigue crack front.

Fracture Toughness Evaluation

FEM Analysis for Mullite Specimens

Material properties of mullite and FEM used in the analysis are tabulated in Table 1. Cursory verifications of crack propagation orientation were done by visual inspection. Results appear to support the assumptions, and the selection of the FEM seems appropriate.

Due to the finite length and end grips of the specimen, the stress and strain distributions under pure torsion are not uniform throughout the length, but the mid-length portion is reasonably uniform. Since a zero axial load is maintained during torsion, the specimen is permitted to deform freely along the axis. For all practical purposes, this condition can be simulated for the middle layer elements of FEM, and was used as the FEM boundary condition.

TABLE 1

Material properties and criteria used in FEM analysis

| | Material Property (RT) | FEM* | Loading Condition |
|---|---|---|---|
| Mullite Ceramic | Flexural strength = 186 MPa, E = 155 GPa, $\nu$ = 0.25, $\rho$ = 2800 kg/m$^3$, Vendor $K_{IC}$ = 2.2 MPa$\sqrt{m}$. | 17-mm dia. X 7.6-mm long circular bar**, smallest mesh size = 0.0127-mm | Fracture load: end rotation = 0.000702 rad |
| A302B Steel | Yield stress (tran.) = 500 MPa, Yield stress (long.) = 533 MPa, UTS = 682 MPa, E = 206.8 GPa, $\nu$ = 0.30, CT $K_{IC}$ (TL) = 54.9 MPa$\sqrt{m}$. | 20.3-mm dia. X 7.6-mm long circular bar, smallest mesh size = 0.254 mm | Fracture load: end rotation = 0.00468 rad.. |
| 7475-T7351 Aluminum | Yield stress = 441 MPa, UTS = 517 MPa, E = 70.318 GPa, $\nu$ = 0.33, $\rho$ = 2795 kg/m$^3$, Vendor $K_{IC}$ (TL) = 50.9 MPa$\sqrt{m}$, $K_Q$ (LT) = 56.43 MPa$\sqrt{m}$. | 25.4-mm dia. X 7.6-mm long circular bar**, smallest mesh size = 0.0127-mm | Fracture load: end rotation = 0.009 rad |
| Boundary Condition | One end of the short bar constrained with zero displacements in X and Y axes of the global coordinates, and the other end free. | | |

*3-D 20-node quadratic brick element with reduced integration (3D20R) used in the FEM.
**0.5-mm deep Spiral V-groove with a 45°-pitch, zero root radius.

The torque applied to the specimen was calculated according to the following equation, $$Torque_{END} = \sum_{node\ i}^{n} (R_y * x - R_x * y)_{node\ i}, \quad (15)$$

where $R_x$ and $R_y$ are the reaction forces at the fixed end of FEM in the X-axis and Y-axis directions, respectively, deriving from the LEFM for the fracture loading condition; x and y are the x-and y-components of the distance between the node i and the center of the circular bar, respectively.

Figure 9:
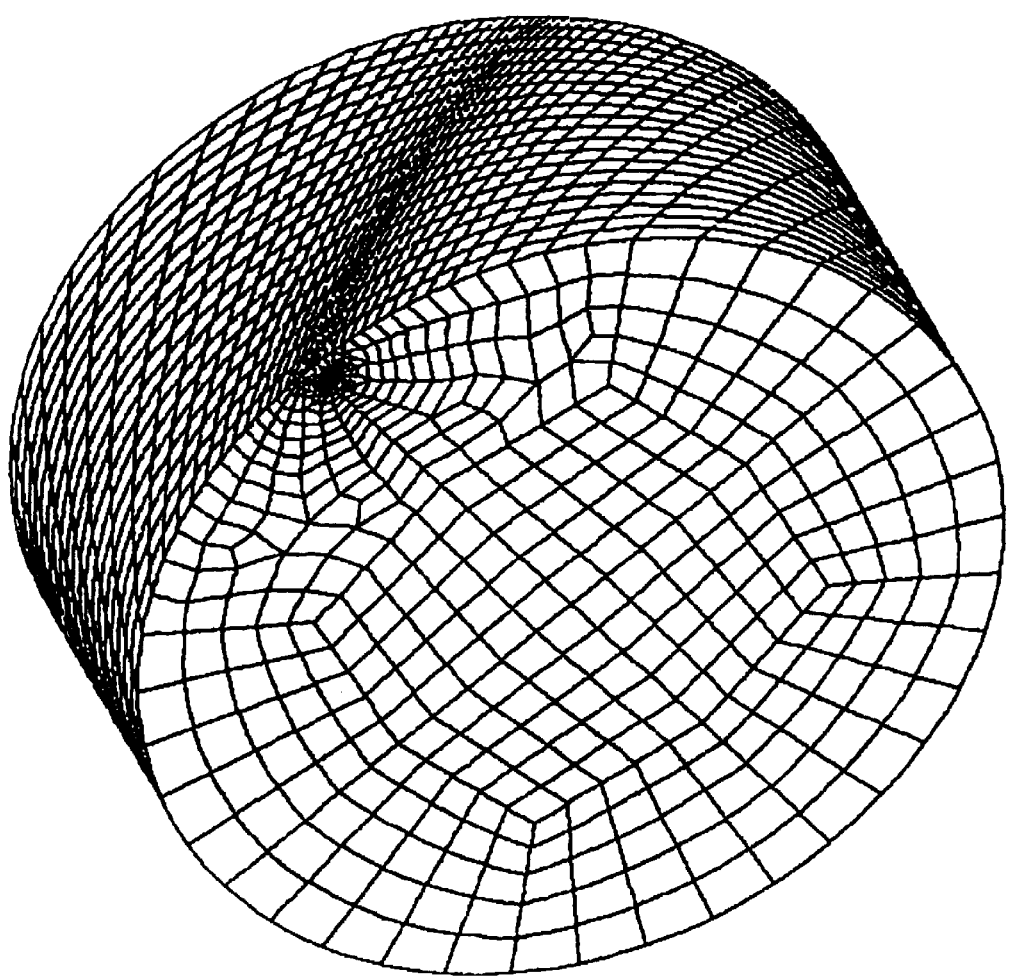
FIG. 9 shows a 3-D finite element model (FEM) mesh with a 0.02-inch deep spiral V-notch for mullite.

The finite element mesh is shown in FIG. 9. The end rotation applied to the FEM at the fracture load of 49.67 N-m was determined by iterative process using Eq. 15. The rotation at the fracture load is estimated to be 0.0007 rad and the J value to be 29.38 N/m at the crack tip. The 3-D FEM analysis indicated that a triaxial tensile state is maintained in front of the crack tip up to the third element from the crack tip. Based on Eq. 4, an evaluation of $\beta$ along the crack flanks can be accomplished using the displacement field in the vicinity of the crack tip. Results indicate $\beta$ is positive and T-stress is positive also, indicating that the high constraint state was achieved.

At the fracture load, the J value at the crack tip in the mid-layer is estimated as 29.38 N/m. Predicted stress intensity factors, according to a COD formulation for the corner node at the crack front of mid-layer, are listed below:

$K_I$=2.098 MPa$\sqrt{\sqrt{m}}$, $K_{II}$=0.0368 MPa$\sqrt{\sqrt{m}}$, $K_{III}$=0.0403 MPa$\sqrt{\sqrt{m}}$.

Corresponding $J_i$ are listed below:

$J_I$=26.62 N/m, $J_{II}$=0.008 N/m, $J_{III}$=0.013 N/m.

The above evaluation indicates 99.9% of the J value is contributed by mode I. According to Eq. 13, the estimate J value is 26.65 N/m, which differs from the evaluated J value 29.38 N/m, from the contour integral, by 9%. This discrepancy may be due to the mesh dependence of COD approach, whereas J-integral value is not so sensitive to the FEM mesh, and seem to be more reliable.

Fracture Toughness $K_{IC}$ Evaluation

Since the crack propagates in the plane normal to the crack front along the X-axis of the local coordinate system, the critical angle $\theta_0$ is equal to zero. Substituting $K_I$, $K_{II}$, $K_{III}$ and $\theta_0$=0 into Eqs. 5 and 8, $K_{IC}$ is estimated to be 2.099 MPa$\sqrt{m}$, which is about 4.5% lower than the vendor's data, 2.2 MPa$\sqrt{m}$.

To determine the upper bound of the $K_{IC}$ value, mode I fracture is assumed to be the dominant component to the J value. This allows an approximate value of plane strain $K_{IC}$ that can be expressed as:

$K_{IC}=\sqrt{EJ/(1-\nu^2)}$=2.205 MPa$\sqrt{m}$.

The approximate $K_{IC}$ value is ~0.2% higher than vendor's data, 2.2 MPa$\sqrt{m}$. Since 99.9% of the J value is from mode I, the estimated $K_{IC}$ from J-integral is more accurate compared to that of the COD approach.

FEM Analysis for A302B Steel Specimens

Figure 10:
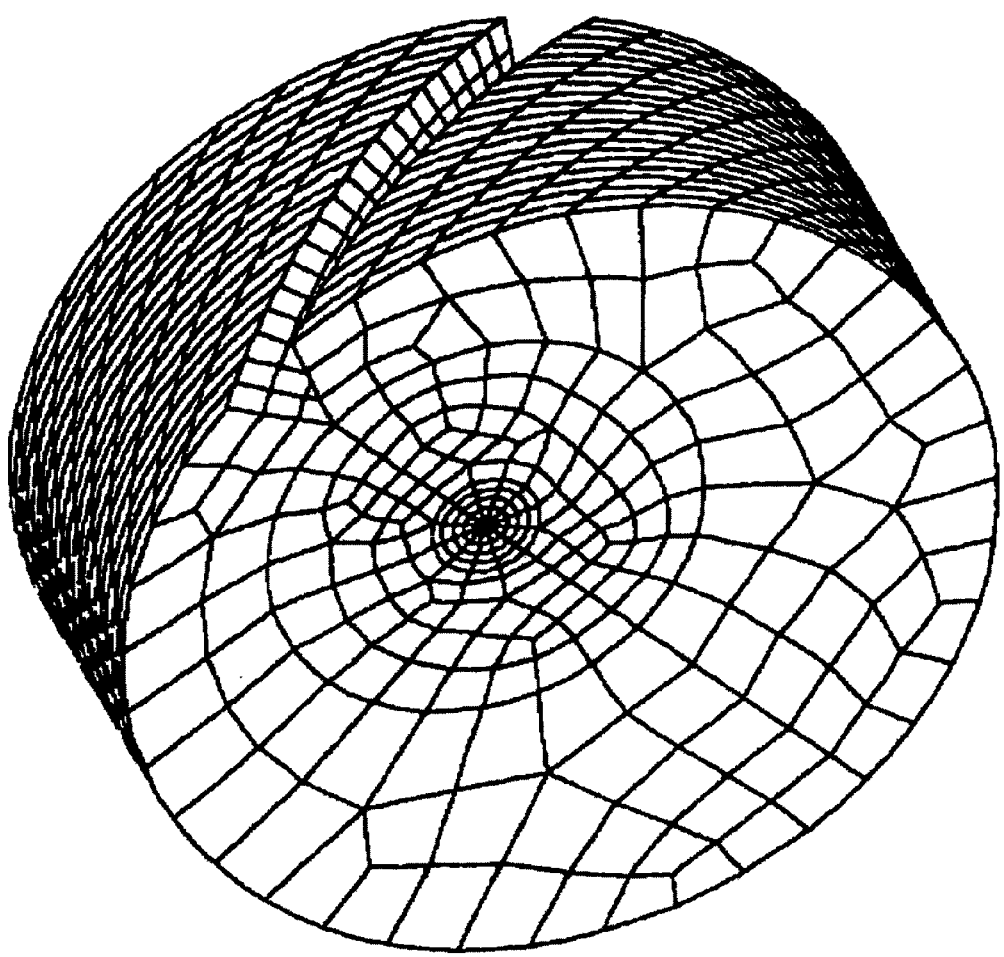
FIG. 10 shows a 3-D FEM mesh with a 0.1-inch deep spiral V-notch and 0.2-inch deep fatigue precrack for A302B steel.

The material properties of the A302B normalized steel and FEM model used in the analysis are shown in Table 1. The fracture configuration with 2.54-mm deep spiral V-groove and 5.08-mm deep fatigue precrack was analyzed. The finite element mesh is shown in FIG. 10. The end rotation applied to the FEM at the fracture load of 519 N-m was determined by iterative process using Eq. 15. The rotation at the fracture load is estimated to be 0.00468 rad, and the J-integral value to be 13.71 KN/m at the crack tip. An upper bound of $K_{IC}$ value is estimated from J-integral value as 55.8 MPa$\sqrt{m}$ which is ~1.6% higher than 54.9 MPa$\sqrt{m}$ obtained for CT specimens.

FEM Analysis for 7475-T7351 Aluminum Specimens

Figure 11:
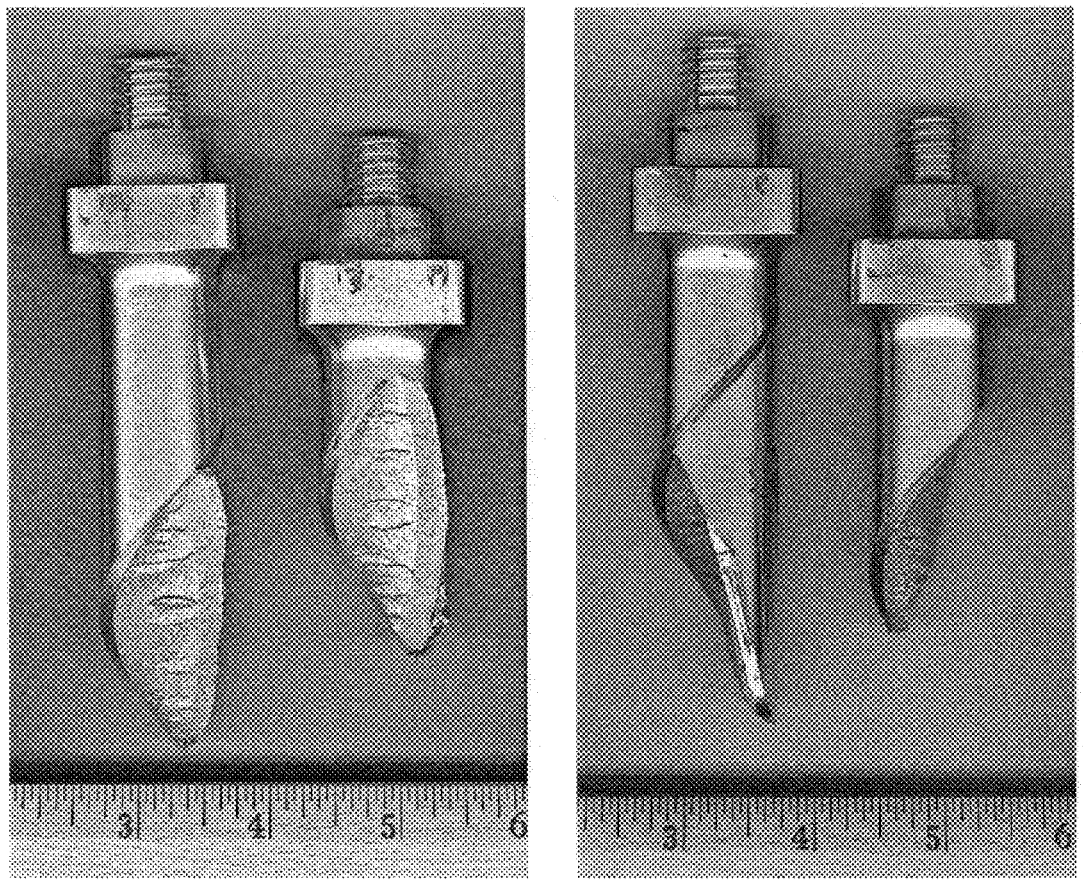
FIG. 11 shows a broken 7475 T7351 aluminum specimen with 0.1-inch deep spiral V-notch and 0.708-inch deep fatigue precrack.

Material properties of 7475-T7351 aluminum alloy and FEM model used in the analysis are tabulated in Table 1. Cursory verifications of crack propagation orientation were done by visual inspection, see FIG. 11. Results appear to support the assumptions, and the selection of the finite element model (FEM) seems appropriate. Due to the finite length and end grips of the specimen, the stress and strain distributions under pure torsion are not uniform throughout the length, but the mid-length portion is reasonably uniform. Since a zero axial load is maintained during torsion, the specimen is permitted to deform freely along the axis. For all practical purposes, this condition can be simulated for the middle layer elements of FEM with the use of the proposed boundary condition.

To model the crack extension during the fatigue precrack, three different configurations of FEM were generated, namely, (1) FEM with 2.5-mm deep V-groove but no fatigue precrack, (2) FEM with 2.54-mm deep V-groove plus 2.54-mm deep fatigue precrack, and (3) same as (2) with a 5.08-mm deep fatigue precrack. A detailed FEM analysis for each case is described below.

1. FEM Results for Shallow Crack (with 0.254 cm Deep Spiral V-notch)

A 3-D tensor plot of the principal stresses along the crack propagation orientation shows that a triaxial tensile state is maintained in front of the crack tip up to the fifth element from the crack tip. The triaxial tensile state near the crack tip was also revealed from results of a non-linear finite element analysis using the small strain criterion. The strain field $\epsilon_{zz}$, tangential to the crack front, appears to be negative throughout the middle layer of FEM. The contours of $\epsilon_{zz}$ form a very narrow band near the crack tip, which is symmetrical with respect to the X-axis. Near the crack tip, the absolute magnitude of the $\epsilon_{zz}$ strain field along the crack propagation orientation shows to be one order of magnitude smaller than that in Y-axis (normal) orientation.

2. FEM Results for Intermediate Crack Length Configuration (with 2.54-mm Deep Spiral V-notch and 2.54-mm Deep Fatigue Precrack)

2.1 Type II Mesh

To conform the "maximum principal stress criterion," which assumes the crack to propagate perpendicularly to the maximum principal stress, Type II mesh is selected for FEM. At the maximum load, the calculated J value at the crack tip in the mid-layer is 5.95 KN/m. The strain field in the local coordinate system was used in Eq. 8 to calculate $K_I$ as listed below:

$K_I$=21.85 MPa√m, $K_{II}$=1.850 MPa√m, $K_{III}$=0.465 MPa√m.

Corresponding $J_i$ are listed below:

$J_I$=6.05 KN/m, $J_{II}$=0.044 KN/m, $J_{III}$=0.004 KN/m.

The above evaluation indicates ~99.2% of the J value is contributed by mode I. According to Eq. 13, the J can be estimated as 6.09 KN/m, which differs from the ABAQUS value by ~2.4%.

Based on Eq. 4, an evaluation of β along the crack flanks can be accomplished using the displacement field in the vicinity of the crack tip. Results indicate β is positive and T-stress is positive also, indicating that the high constraint state was achieved in the specimen with a 2.54-mm-deep spiral V-groove and a 2.54-mm-deep fatigue precrack.

2.2 Type I Mesh

Type I finite element mesh was used in the analysis. A triaxial tensile state is indicated in the elements near the crack tip and extending out to the $7^{th}$ element from the crack front.

The J-integral value near the crack tip was evaluated under incremental loading, using a non-linear analysis method based on the small-strain criterion. The size effect on opening mode stress near the crack tip at a constant normalized distance R, R=r/(J/$\sigma_0$), leading ahead of the crack can be investigated approximately with the Kirk-Dodds-Andersons formula. For illustrative purposes, $\sigma_0$ is set to equal the yield stress, 441 MPa. The normalized load is set to 1 at the maximum load (load case 1). The opening-mode stresses corresponding to seven normalized loads at R=2 were calculated from the stress contours and tabulated in Table 2. A monotonic increase of the opening mode stresses with increasing load is observable from Table 2. Substituting the values in Eq. 3 will show that the biaxial factor β is positive; therefore, the high constraint state is achieved in this crack configuration.

TABLE 2

Opening mode stress near the crack tip at a constant normalized distance R = 2.

| Normalized Load | J-integral KN/m | Distance r mm | Opening Mode Stress $\sigma_{yy}$ MPa | Normalized Stress $\sigma_{yy}$ |
|---|---|---|---|---|
| 0.100 | 0.144 | 0.00065 | 912 | 2.067 |
| 0.200 | 0.574 | 0.0026 | 1090 | 2.471 |
| 0.350 | 1.75 | 0.0080 | 1175 | 2.664 |
| 0.575 | 4.78 | 0.0217 | 1206 | 2.734 |
| 0.912 | 12.0 | 0.0540 | 1206 | 2.734 |
| 1.000 | 14.5 | 0.0657 | 1212 | 2.746 |

3. FEM Results for Final Fracture Configuration (with 2.54-mm Deep Spiral V-groove and 5.08-mm Deep Fatigue Precrack)

3.1 $K_{IC}$ Evaluated from Type I Mesh FEM

Figure 13:
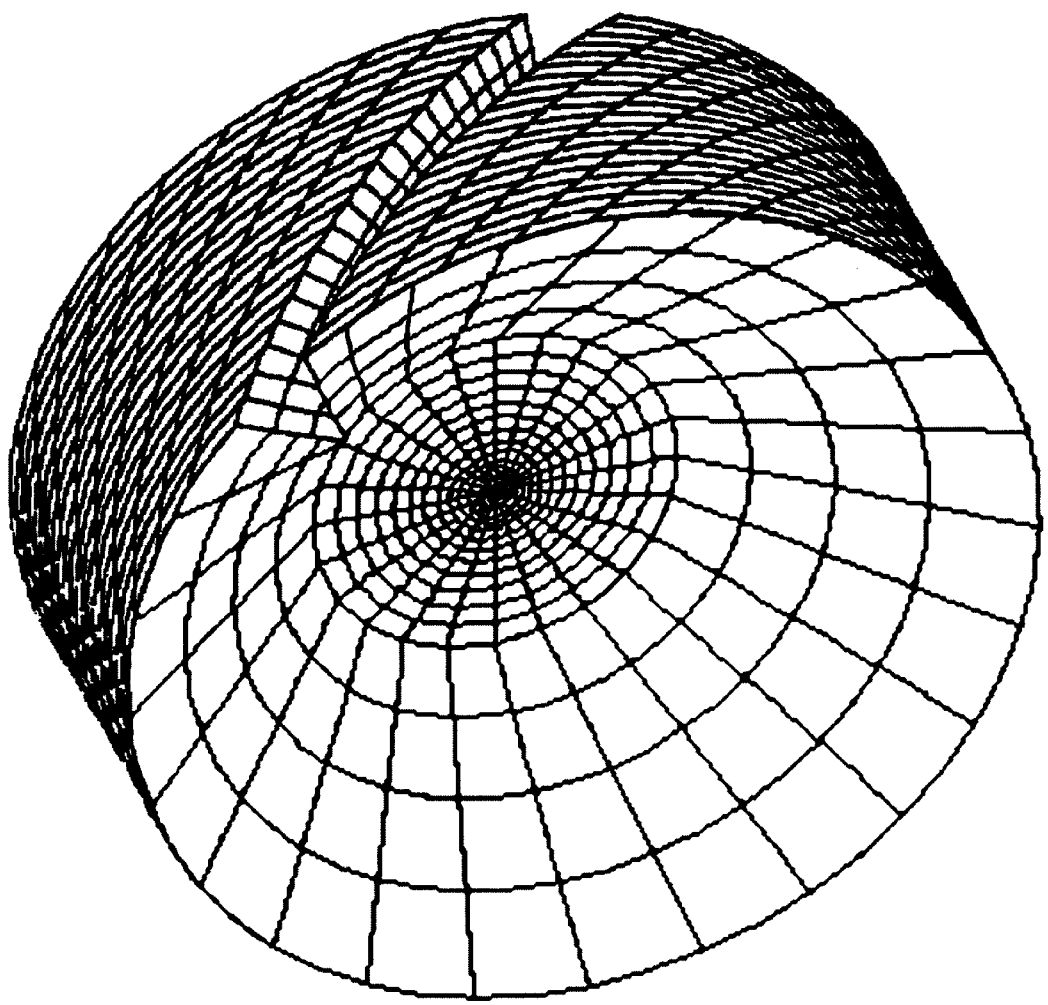
FIG. 13 shows a 3-D FEM mesh with a 0.1-inch deep spiral V-notch and 0.2 inch deep fatigue precrack for 7475 T7351 aluminum alloy.
Figure 14:
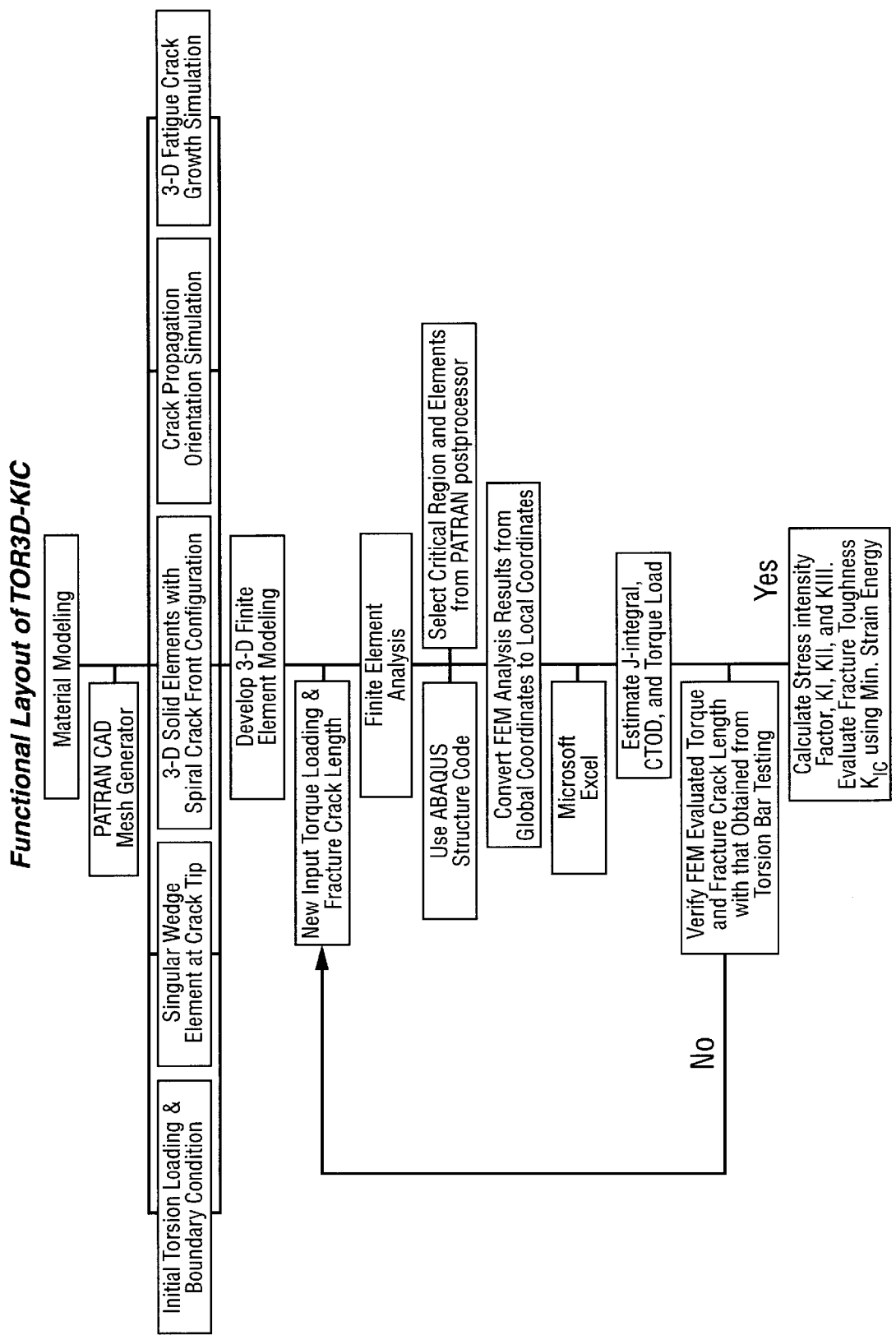
FIG. 14 is a flow chart showing the fracture toughness determination steps of the invention. The steps shown are for the determination of $K_{IC}$.

Type I finite element mesh was used in the analysis and the FEM is shown in FIG. 13. The end rotation applied to the FEM at the fracture load of 948 N-m was determined by an iterative process using Eq. 15. The rotation at the fracture load is estimated to be 0.009 rad and J value to be 33.8 KN/m at the crack tip. To determine the upper bound of $K_{IC}$ value, mode I fracture is assumed to be the dominant component to the J value. This allows an approximate value of plane strain $K_{IC}$ that can be expressed as:

$K_{IC}=\sqrt{EJ/(1-\nu^2)}=51.64$ MPa√m.

The approximate $K_{IC}$ value is ~6% higher than 48.3 MPa√m obtained for 0.5 CT.

3.2 $K_{IC}$ Evaluated from Type II Mesh FEM

A Type II finite element mesh with case 2 loading was analyzed. Results reveal that a triaxial tensile state was indicated near the crack tip and to the $8^{th}$ element from the crack front. Predicted stress intensity factors for the corner node at the crack front of mid-layer, are listed below:

$K_I$=47.3 MPa√m, $K_{II}$=0.73 MPa√m, $K_{III}$=11.6 MPa√m.

Since the crack propagates in the plane normal to the crack front along the X-axis of the local coordinate system, the critical angle $\theta_0$ is equal to zero. Substituting $K_I$, $K_{II}$, $K_{III}$ and $\theta_0$=0 into Eqs. 6 and 8, $K_{IC}$ is estimated to be 51.3 MPa√m.

Some of the noteworthy features of the present invention are:

1) The stress and strain fields under pure torsion of a cylindrical specimen are a function of radius only, and are the same everywhere along the notch line. The length of the spiral crack, equivalent to the thickness of a compact tension specimen, is limited only by the length of the specimen. Thus, the size effect that is normally a concern in compact type specimens is minimized.

2) Failures in any combined mixed mode can be tailored by varying the pitch angle of the starting notch line. Commonly, the materials fracture in mixed modes rather than in a single mode; and in many cases, a combination of mode I and mode III are more critical than mode I alone.

3) The proposed testing method will confine most of the plastic deformation that controls the $K_{IC}$ fracture toughness to a narrow plane. With the ability of conducting focused sampling on a thin plane and controlled crack propagation orientation on a sample specimen, it will be possible to determine the $K_{IC}$ values of interfaces of inhomogeneous materials and material properties in the HAZ of weldments.

While there has been shown and described what are at present considered the preferred embodiments of the invention, it will be obvious to those skilled in the art that various changes and modifications can be prepared therein without departing from the scope of the inventions defined by the appended claims.

We claim:

1. A method of determining fracture toughness $K_{IC}$ of a material comprising the steps of:
    a) providing a cylindrical specimen having a helical groove at a 45° pitch angle with respect to the specimen axis;
    b) applying pure torsional loading to the specimen axis;
    c) measuring the torque at fracture;
    d) measuring the crack length; and
    e) calculating $K_{IC}$ from the fracture torque and the crack length.

2. The method of claim 1 wherein the specimen is a brittle material.

3. The method of claim 1 wherein the specimen is a ductile material.

4. The method of claim 3 wherein the helical groove is a V-shaped groove.

5. The method of claim 4 wherein the V-shaped groove has been subjected to a precracking treatment.

6. The method of claim 1 wherein the specimen is a weldment.

7. The method of claim 6 wherein the helical groove is located on the weldment.

8. The method of claim 6 wherein the helical groove is located on the heat affected zone of the weldment.

9. The method of claim 1 wherein the helical groove is at least a one-half turn helical groove.

10. The method of claim 1 wherein the specimen has square ends.

11. The method of claim 1 wherein the specimen is cohesively bonded to an end holder.

12. The method of claim 1 wherein the fracture torque is measured with an axial/torsional biaxial load cell.

13. The method of claim 1 wherein the crack length is measured with an axial/torsional biaxial extensometer.

14. The method of claim 1 wherein the crack length is measured with a rosette strain gage.

15. The method of claim 1 wherein the calculation of $K_{IC}$ is carried out with a computer program.

16. The method of claim 15 wherein the computer program comprises the steps of:
    a) establishing a finite element mesh for a cylindrical specimen under pure torsion to generate an equibiaxial tension/compression stress field on ±45°-pitched orthogonal planes of the finite elements along the right conoids, and a plane strain condition is maintained on every plane normal to the helical groove;
    b) establishing 3-D isoparametric finite element meshes with singular elements around the 3-D spiral crack front to simulate $r^{-\frac{1}{2}}$ singularity at the crack tip;
    c) simulating spiral crack front and crack propagation orientation along the right conoids;
    d) prescribing boundary conditions with free axial displacement to simulate pure torsion loading;
    e) applying initial end rotation to the finite element model with a given final crack length to determine the corresponding end torque;
    f) iterating step e. to match the end torque with the measured fracture torque to determine the final end rotation of the finite element model;
    g) determining the crack tip opening displacement based on the stress/strain field derived from the final end rotation calculated in step f;
    h) verifying that the triaxial stresses and T-stress fields around the crack tip at fracture are positive to ensure a high constraint state is achieved;
    i) determining stress intensity factors $K_I$, $K_{II}$, and $K_{III}$ based on the crack tip opening displacement obtained from step g); and
    j) utilizing information gained from step i) and strain energy density criteria to determine the fracture toughness $K_{IC}$.

17. A method of determining mixed mode fracture toughness of a material comprising the steps of:
    a) providing a cylindrical specimen having a helical groove at a pitch angle other than 45° with respect to the specimen axis;
    b) applying pure torsional loading to the specimen axis;
    c) measuring the torque at fracture;
    d) measuring the crack length; and
    e) calculating the mixed mode fracture toughness from the fracture torque and the crack length.

18. The method of claim 17 wherein the specimen is a brittle material.

19. The method of claim 17 wherein thee specimen is a ductile material.

20. The method of claim 19 wherein the specimen is a weldment.

21. The method of claim 20 wherein the helical groove is located on the weldment.

22. The method of claim 19 wherein the helical groove is a V-shaped groove.

23. The method of claim 22 wherein the V-shaped groove has been subjected to a precracking treatment.

24. The method of claim 20 wherein the helical groove is located on the heat affected zone of the weldment.

25. The method of claim 17 wherein the helical groove is at least a one-half turn helical groove.

26. The method of claim 17 wherein the specimen has square ends.

27. The method of claim 17 wherein the specimen is cohesively bonded to an end holder.

28. The method of claim 17 wherein the fracture torque is measured with an axial/torsional biaxial load cell.

29. The method of claim 17 wherein the crack length is measured with an axial/torsional biaxial extensometer.

30. The method of claim 17 wherein the crack length is measured with a rosette strain gage.

31. The method of claim 17 wherein the calculation of mixed mode fracture toughness is accomplished with a computer program.

32. The method of claim 31 wherein the computer program comprises the steps of:
    a) establishing a finite element mesh for a cylindrical specimen under pure torsion to generate an equibiaxial tension/compression stress field on ±45°-pitched orthogonal planes of the finite elements along the right conoids, and a plane strain condition is maintained on every plane normal to the helical groove;

b) establishing 3-D isoparametric finite element meshes with singular elements around the 3-D spiral crack front to simulate $r^{-1/2}$ singularity at the crack tip;

c) simulating spiral crack front and crack propagation orientation along the right conoids;

d) prescribing boundary conditions with free axial displacement to simulate pure torsion loading;

e) applying initial end rotation to the finite element model with a given final crack length to determine the corresponding end torque;

f) iterating step e. to match the end torque with the measured fracture torque to determine the final end rotation of the finite element model;

g) determining the crack tip opening displacement based on the stress/strain field derived from the final end rotation calculated in step f;

h) verifying that the triaxial stresses and T-stress fields around the crack tip at fracture are positive to ensure a high constraint state is achieved;

i) determining stress intensity factors $K_I$, $K_{II}$, and $K_{III}$ based on the crack tip opening displacement obtained from step g); and j) utilizing information gained from step i) and strain energy density criteria to determine the mixed mode fracture toughness.

* * * * *